United States Patent [19]

Urry

[11] 3,992,472
[45] Nov. 16, 1976

[54] SYNTHESIS OF ETHYLENICALLY UNSATURATED COMPOUNDS FROM ALDEHYDES OR KETONES

[75] Inventor: Grant Wayne Urry, Winchester, Mass.

[73] Assignee: E. I. Du Pont de Nemours and Company, Wilmington, Del.

[22] Filed: July 18, 1975

[21] Appl. No.: 597,142

[52] U.S. Cl. ............................ 260/682; 260/429 R; 260/666 R; 260/666 A; 260/668 B; 260/669 QZ; 260/677 R
[51] Int. Cl.² .......................................... C07C 1/20
[58] Field of Search ........ 260/666 A, 666 R, 668 B, 260/669 QZ, 677 R, 429, 682

[56] References Cited
UNITED STATES PATENTS

| | | | |
|---|---|---|---|
| 3,013,068 | 12/1961 | De La Mare et al. | 260/682 |
| 3,156,739 | 11/1964 | Horner et al. | 260/682 |
| 3,277,202 | 10/1966 | Benson et al. | 260/666 A |
| 3,644,559 | 2/1972 | Kobylinski et al. | 260/666 A |

OTHER PUBLICATIONS

A. William Johnson, Ylid Chemistry, pp. 132–192, Academic Press, N.Y., 1966.

Primary Examiner—Veronica O'Keefe
Attorney, Agent, or Firm—Anthony P. Mentis

[57] ABSTRACT

Certain hydrocarbylidene-niobium or -tantalum complexes react with aldehydes or ketones to produce ethylenically unsaturated compounds. Exemplary is the reaction of trineopentyl(neopentylidene)tantalum with acetone to produce 2,4,4-trimethyl-2-pentene:

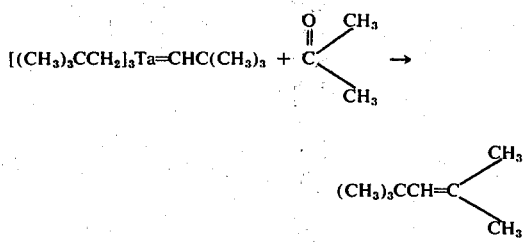

12 Claims, No Drawings

SYNTHESIS OF ETHYLENICALLY UNSATURATED COMPOUNDS FROM ALDEHYDES OR KETONES

BACKGROUND OF THE INVENTION

1. Field of the Invention

This invention is the reaction of certain hydrocarbylideneniobium or hydrocarbylidenetantalum complexes with aldehydes or ketones to produce ethylenically unsaturated compounds.

2. Prior Art

It is known to react a phosphonium ylid with an aldehyde or ketone to give an olefin; A. W. Johnson "Ylid Chemistry", pp. 132–192 (Academic Press 1966), but no reference appears to exist with respect to the use of a niobium or tantalum complex for such reaction.

SUMMARY OF THE INVENTION

The invention is the process of reacting a metal compound of the formula

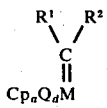

in which
Cp is a $\pi$-cyclopentadienyl group having up to one alkyl substituent of 1–10 carbons;
Q is alkyl of 1–10 carbons, aralkyl of 7–10 carbons or diarylmethyl of 13–21 carbons in which the $\beta$-carbon is not bonded to hydrogen;
M is niobium or tantalum;
$R^1$ and $R^2$ individually are hydrogen, tertiary alkyl of 4–10 carbons or aryl of 6–10 carbons;
$a$ is 0 or 2;
$d$ is 1 or 3; and
$a$ plus $d$ equals 3;
with an organic carbonyl compound of the group consisting of an aldehyde and a ketone, said carbonyl compound being free of Zerewitinoff-active hydrogen and any multiple bond present other than that in the carbonyl group being a carbon to carbon multiple bond or a multiple bond contained in an aromatic heterocyclic ring, at a temperature in the range of 0°–250° C, and in the substantial absence of oxygen and moisture to produce an ethylenically unsaturated compound. As is known, a compound that reacts with a Zerewitinoff reagent to produce methane is considered to have Zerewitinoff-active hydrogen. The reaction can be exemplified by the equation

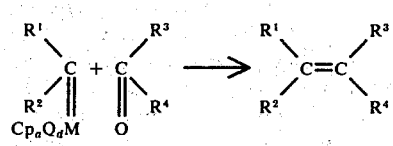

The fate of the $Cp_aQ_dM$ moiety is not known.

The reaction is a broad one in that any aldehyde or ketone, of whatever size or complexity, will work in the reaction so long as it conforms to the criteria stated above. The process produces olefins or ethylenically unsaturated compounds.

So long as the carbonyl compound as a whole satisfies the criteria mentioned, $R^3$ and $R^4$ can be hydrogen or any organic group and include alkyl, alkenyl, alkynyl, cycloalkyl, cycloalkenyl or aryl, and groups containing more than one such structure, as alkylcycloalkyl, alkaryl, aralkyl and the like. Since the groups can contain double and triple bonds, the process can produce not only monoethylenically unsaturated compounds but also dienes, enynes and the like.

The groups can also contain one or more hetero atoms and can therefore include substituents such as hydrocarbyloxy, hydrocarbylthio and dihydrocarbylamino, as for example, oxaalkyl, thiaalkyl, azaalkyl and alkenyl, alkynyl, cycloalkyl and aryl correspondingly containing a hetero atom. Thus the groups can contain or be composed of units derived, for example, from tetrahydrofuran, tetrahydrothiophene, piperidine, furan, thiophene, or pyridine. In any units derived from piperidine or other cyclic secondary amines there would be no hydrogen on the nitrogen, e.g., as in 2-piperidinoethyl. For convenience in naming, groups such as alkyl, alkenyl, cycloalkyl and aryl containing one or more hetero atoms in the carbon skeletons can be designated here as heteraalkyl, heteraalkenyl, heteracycloalkyl and heteraaryl groups, respectively. Examples, also respectively, are 2-methoxyethyl, 2-vinyloxyethyl, 3-tetrahydrothienyl, and 4-pyridyl. Substituents also include halo groups, i.e., fluoro, chloro, bromo, and iodo. Any halo substituent should be on a carbon separated from the carbonyl carbon by at least one other carbon.

Because of availability and in some cases of reactivity, preferred aldehydes have the formula

wherein $R^5$ is hydrogen, alkyl of 1–8 carbons, alkenyl of 2–8 carbons, aryl of 6–12 carbons or alkaryl of 7–12 carbons, each having up to one substituent of halo, alkoxy of 1–6 carbons, alkylthio of 1–6 carbons or dialkylamino each alkyl having 1–6 carbons.

Ketones which are presently preferred for reasons of availability or reactivity have the formula

wherein $R^6$ and $R^7$ individually are alkyl of 1–8 carbons, alkenyl of 2–8 carbons, aryl of 6–12 carbons or alkaryl of 7–12 carbons, each having up to one substituent of halo, alkoxy of 1–6 carbons, alkylthio of 1–6 carbons, or dialkylamino each alkyl having 1–6 carbons, and $R^6$ and $R^7$ can together form an alkylene group of 3 to 8 carbons.

More preferred ketones are the compounds where the alkyl and alkenyl groups are primary or secondary.

Most preferred are the compounds where $R^5$, $R^6$ and $R^7$ contain no substituents.

Representative carbonyl compounds include formaldehyde, acetaldehyde, propionaldehyde, butyraldehyde, valeraldehyde, hexanal, heptanal, octanal, 5-hexenal, 2-butynal, crotonaldehyde, 2-ethylhexanal, 3-diethylaminopropanal, benzaldehyde, 2-chlorobenzaldehyde, 3-biphenylcarboxaldehyde, 6-propylthiohexanal, 4-cyclohexylbutanal, 3-pyridinecarboxaldehyde, octadecanal, 6-fluorohexanal, 4-t-butylbenzaldehyde, acetone, cinnamaldehyde, 2-butanone, cyclohexanone, 3-methylacetophenone, cyclooctanone, 3-ethylcyclohexanone, 3-cyclohexenone, 9-heptadecanone, 3-pentynone, 8-methoxy-2-octanone, ethyl 3-tetrahydrothienyl ketone, 1-naphthyl propyl ketone, 1-bromo-4-heptanone, 4-iodopropiophenone, acrylophenone, cyclohexyl methyl ketone, 3-dipropylaminobenzophenone, and the like.

The process can be carried out in the presence or absence of a solvent. Useful solvents include ethers, such as ethyl ether, tetrahydrofuran, dioxane, 1,2-dimethoxyethane, and 2-methoxyethyl ether, and hydrocarbons such as pentane, hexane, heptane, cyclohexane, benzene, toluene, and petroleum ether. When an excess of carbonyl compound is used and the compound is a suitable liquid, the excess carbonyl compound can function as solvent. The niobium- and tantalum-containing starting materials are usually prepared in ether or hydrocarbon solvents, and if desired, solutions thus obtained can be used directly in the present process without isolation of the starting material.

The reactant ratio, temperature, and time can be varied, depending on the nature of the reactants.

Niobium- and tantalum-containing starting materials in which $a$ is 0 and $d$ is 3 can be written as $Q_3M=CR^1R^2$. With such starting material, the reaction is essentially instantaneous at about 25° C with a 1:1 mole ratio of reactants, but any temperature in the range of about 0°–150° C or even higher can be used.

Metal-containing starting materials in which $a$ is 2 and $d$ is 1, which can be formulated as $Cp_2QM=CR^1R^2$, react more slowly than the $Q_3M=CR^1R^2$ type, and the latter are therefore preferred. For example, several hours at temperatures averaging about 50° C or higher may be required. Again, higher carbonyl:organometallic ratios, e.g., from about 10:1 to 100:1 or even higher, help speed up the process.

For less reactive systems higher temperatures can be used.

In all the foregoing embodiments, pressure is not a particularly critical variable. Usually, the process is conducted at atmospheric pressure for convenience. When the process is conducted near or above the boiling point of the carbonyl compound, it is customary to operate at the autogeneous pressure developed in a closed system. The course of the reaction can usually be followed by observing the precipitation of the niobium- or tantalum-containing by-product.

The niobium- or tantalum-containing starting materials can be prepared according to the procedures set out in copending application (docket number CR 7523-A, Ser. No. 570,259) filed on or about Apr. 21, 1975, in the name of Richard R. Schrock. That application discloses three methods for preparing starting materials of the formula $$Q_3M=CR^1R^2$$

where $a$ is zero and $d$ is 3 as follows.

In the first method, a trihydrocarbylmetal dichloride, $Q_3MCl_2$, such as trineopentyltantalum dichloride or trineopentylniobium dichloride is reacted with two moles of a hydrocarbyllithium compound in which the hydrocarbyl group corresponds to the hydrocarbylidene group in the product:

1. 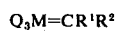 $(C_5H_{11})_3MCl_2 + 2LiCHR^1R^2 \rightarrow (C_5H_{11})_3M = CR^1R^2 + CH_2R^1R^2 + 2LiCl$ In the second method, four moles of a hydrocarbyllithium, QLi, such as neopentyllithium are reacted with one mole of a hydrocarbyltantalum tetrachloride or hydrocarbylniobium tetrachloride in which the hydrocarbyl group corresponds to the hydrocarbylidene group in the product:

2. $4C_5H_{11}Li + Cl_4MCHR^1R^2 \rightarrow (C_5H_{11})_3M=CR^1R^2$ 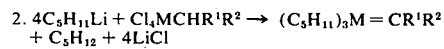 $+ C_5H_{12} + 4LiCl$ The ultimate source of tantalum or niobium in each of these three processes is tantalum pentachloride or nioniobium pentachloride. In the third method, a trihydrocarbyl(hydrocarbylidene)tantalum compound such as trineopentyl(neopentylidene)tantalum is prepared directly from $TaCl_5$ by reacting it with five moles of an appropriate hydrocarbyl Grignard reagent such as neopentylmagnesium chloride:

3. $TaCl_5 + 5C_5H_{11}MgCl \longrightarrow (C_5H_{11})_3Ta = CHC(CH_3)_3 + 5MgCl_2 + C_5H_{12}$ 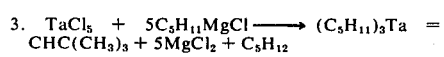

The corresponding niobium compounds can be similarly prepared from $NbCl_5$.

Starting materials of the formula $$Cp_2QM=CR^1R^2$$

where $a$ is 2 and $d$ is 1 are prepared by reacting an appropriate dihydrocarbylmetal trihalide with two moles of cyclopentadienylthallium:

4. 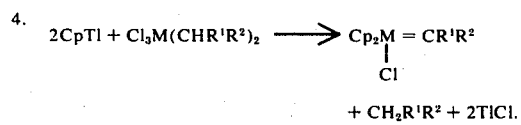

The product of the equation (4) can then be reacted with an appropriate hydrocarbyllithium, or preferably a diamine complex thereof, for example, according to equation (5):

5. 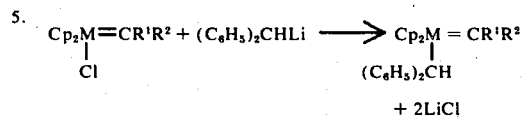

Examples of alkyl groups that can be substituents in the cyclopentadienyl ring are methyl, ethyl, isopropyl, t-butyl, hexyl, octyl and decyl. Because of the commercial availability of cyclopentadiene and methylcyclopentadiene, the cyclopentadienyl and methylcyclopentadienyl groups are preferred. Examples of suitable groups are thus cyclopentadienyl, methylcyclopentadienyl, ethylcyclopentadienyl, isopropylcyclopentadienyl, t-butylcyclopentadienyl, hexylcyclopentadienyl, octylcyclopentadienyl and decylcyclopentadienyl.

Examples of Q are methyl, neopentyl, 2,2,4,4-tetramethyl-3-pentyl, benzyl, p-ethylbenzyl, naphthylmethyl, $\beta,\beta$-dimethylphenethyl ("neophyl"), diphenylmethyl, and ditolylmethyl. A preferred class of Q groups comprises alkyl and aralkyl and most preferably Q is methyl, neopentyl or benzyl.

Examples of tertiary alkyls for $R^1$ and $R^2$ are tertiary butyl, tertiary pentyl, tertiary hexyl, tertiary heptyl, tertiary octyl, tertiary nonyl and tertiary decyl.

"Aryl" and "ar" are used herein to denote a radical derived from a hydrocarbon having as its only unsaturation aromatic unsaturation in six-membered carbocyclic rings by removal of a hydrogen atom from a carbon atom in such an aromatic ring. Examples of aryl groups are phenyl, 1- and 2-naphthyl, o-, m- and p-tolyl, ethylphenyl, butylphenyl, xylyl, and trimethylphenyl.

Exemplary of the preparation of these compounds are the following, in which the reaction is carried out in an atmosphere of dry nitrogen.

EXAMPLE A

Trineopentyl(neopentylidene)tantalum

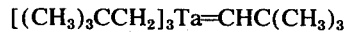

A. A solution of 0.5 g of trineopentyltantalum dichloride and 0.17 g of neopentyllithium in 4 ml of pentane was allowed to stand at room temperature for 24 hr in a glass vessel wrapped in foil. (In later experiments it was found that the foil wrapping was unnecessary.) The lithium chloride that had precipitated was separated by filtration, and the filtrate was allowed to stand for another 24 hr at room temperature. No more solid precipitated during this time. Volatile materials were removed under reduced pressure to give trineopentyl(neopentylidene)tantalum, $(C_5H_{11})_3Ta=C_5H_{10}$, as an orange crystalline solid.

An $^1H$ nmr of the product in $C_6D_6$ showed four singlets in the ratio 1:9:27:6 at $\tau 8.09$ (1), $\tau 8.57$ (9), $\tau 8.85$ (27), and $\tau 9.16$ (6).

B. The foregoing procedure was essentially repeated (24-hr reaction period) with double quantities of materials to give 0.85 g (85%) of $(C_5H_{11})_3Ta=C_5H_{10}$. The product was combined with the product from part A, and the mixture was heated in a sublimation apparatus at 80° C/0.5μ. The crystals thus obtained on the cold finger had the same appearance and the same $^1H$ nmr as the original product. A mass spectrum showed a peak at m/e 464.

C. A solution of 5.15 g of $(C_5H_{11})_3TaCl_2$ and 1.75 g of $C_5H_{11}Li$ in 50 ml of pentane was allowed to stand at room temperature for eight hours, and the lithium chloride that precipitated was removed by filtration. When the volume of the filtrate was reduced to about 5 ml under reduced pressure without heating, orange crystals precipitated; they redissolved when the mixture was allowed to warm to room temperature. The mixture was filtered, and the filtrate was kept overnight at −30° C. No crystals appeared. The volume of the solution was reduced from 6 ml to 4 ml, and the solution was allowed to stand overnight again at −30° C. The orange crystals of $(C_5H_{11})_3Ta=C_5H_{10}$ that appeared were separated by filtration; yield 2.5 g. Removal of the rest of the solvent under reduced pressure gave an additional 1.8 g of product. The total yield was 84%.

Anal. calcd. for $C_{20}H_{43}Ta$: C, 51.72; H, 9.33; Ta, 38.95; mol wt, 464 Found: C, 51.39; H, 9.31; Ta, 41.22; mol wt, 472 51.09 9.24 42.77 50.86 9.22 (cryoscopic in benzene)

EXAMPLE B

Trineopentyl(neopentylidene)tantalum

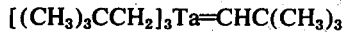

A mixture containing the Grignard reagent prepared from magnesium metal and 160 g of neopentyl chloride in about one liter of ethyl ether was added rapidly with stirring to 107 g of tantalum pentachloride and about one liter of ethyl ether. The mixture was stirred for one hour and filtered, and all volatile material was removed from the filtrate under reduced pressure. The residue was extracted with about 200 ml of pentane, and the filtered extract was evaporated under reduced pressure. The residue was volatilized in a sublimation apparatus at 100° C/1μ to give a total of 75 g (50%; 3 crops) of $(C_5H_{11})_3Ta=C_5H_{10}$ as deep-orange nugget-like crystals; mp 71° C (sealed tube).

EXAMPLE C

Trineopentyl(benzylidene)tantalum

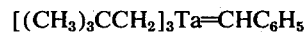

A solution of 2.6 g of $(C_5H_{11})_3TaCl_2$ in 100 ml of hexane was cooled to −78° C, and a solution of 2.4 g of benzyl(N,N,N',N'-tetramethylethylenediamine)lithium in 30 ml of toluene was added dropwise over one hour with rapid stirring. The mixture was warmed to 25° C, stirred for an additional hour, and filtered, and volatile materials were removed from the deep-orange filtrate under reduced pressure, to give an orange residue that contained trineopentyl(benzylidene)-tantalum.

If 4-methylbenzyllithium or a suitable diamine complex thereof is used in place of benzyllithium in essentially the procedure above, trineopentyl(4-methylbenzylidene)-tantalum, $(C_5H_{11})_3Ta=CHC_6H_4CH_3$, will be formed. If 1-naphthylmethyllithium or a complex thereof is used, the product will be trineopentyl(1-naphthylmethylene)tantalum, $(C_5H_{11})_3Ta=CHC_{10}H_7$.

EXAMPLE D

Dicyclopentadienyl(methyl)(methylene)niobium

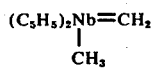

a. $(C_5H_5)_2Nb(CH_3)_3$ was prepared by stirring a mixture of 0.42 g of $(CH_3)_3NbCl_2$, 1.08 g of $C_5H_5Tl$, and about 20 ml of toluene for one hour at room temperature. TlCl was separated by filtration, the filtrate was evaporated in vacuo nearly to dryness, the residue was triturated with pentane, and the mixture was filtered to give 0.28 g of greenish crystals.

$^1H$ nmr ($\tau$, $C_6D_6$): ~5.3 (10, s), ~9.7 (6, s), ~9.8 (3, s).

b. $[(C_5H_5)_2Nb(CH_3)_2]^+BF_4^-$ was prepared by mixing dichloromethane solutions of 0.34 g of $(C_5H_5)_2Nb(CH_3)_3$ and 0.42 g of $(C_6H_5)_3C^+BF_4^-$, whereupon the product precipitated as a yellow solid; yield 0.31 g. $(C_6H_5)_3CCH_3$ was identified in the residue from the filtrate.

$^1H$ nmr ($\tau$. $CD_3CN$): 3.92 (10, s), 9.23 (6, s).

c. $[(C_5H_5)_2Nb(CH_3)_2]^+BF_4^-$ (0.31 g) in ca. 10 ml of tetrahydrofuran was treated with 0.08 g of $(CH_3)_3P=CH_2$. All solids dissolved. The solvent was removed in vacuo and the residue was extracted with pentane. This gave a pentane solution of thermally unstable $(C_5H_5)_2Nb(CH_3)=CH_2$.

SPECIFIC EMBODIMENTS OF THE INVENTION

In the following illustrative examples, all parts are by weight and all degrees are Centigrade unless otherwise stated. All operations at least up to the isolation of the

EXAMPLE 1

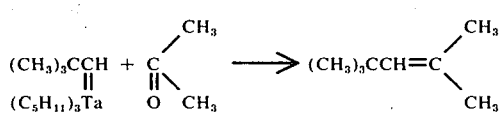

(In this and subsequent examples, $C_5H_{11}$ represents neopentyl, $(CH_3)_3CCH_2$, and $C_5H_{10}$ represents neopentylidene, $CHC(CH_3)_3$).

To a solution of a small quantity of trineopentyl(neopentylidene)tantalum $[(C_5H_{11})_3Ta=C_5H_{10}]$ from Example A in about five times its weight of pentane was added a solution of an equimolar amount of acetone in about three volumes of pentane. The orange color of the tantalum compound immediately disappeared, and a mixture of a pale-yellow liquid and a pale-yellow solid resulted. The solid metal-containing by-product was separated by filtration, and the filtrate was distilled under reduced pressure. The distillate was a mixture of a pentane and 2,4,4-trimethyl-2-pentene. The latter was identified by mass spectroscopy and by comparison with an authentic sample.

Substitution of 3-undecanone for acetone in essentially the foregoing procedure will give 4-ethyl-2,2-dimethyl-3-dodecene as product.

EXAMPLE 2

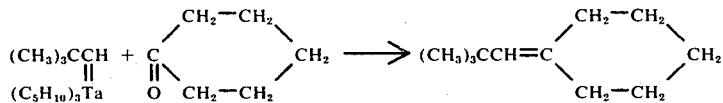

By essentially the method of Example 1, $(C_5H_{11})_3Ta=C_5H_{10}$ was reacted with an equivalent amount of cyclohexanone. The filtrate was analyzed directly, without distillation, by gas chromatography and mass spectroscopy, and shown to contain neopentylidenecyclohexane. The product was identified by mass spectroscopy and by its $^1H$ nmr after isolation by preparative gas chromatography. $^1H$ nmr (CDCl$_3$): τ4.83 (m,1), τ7.5–8.7 (m,10), τ8.90 (s,9).

Neopentylidenecyclononane can be obtained by substituting cyclononanone for cyclohexanone in essentially the foregoing procedure.

EXAMPLE 3

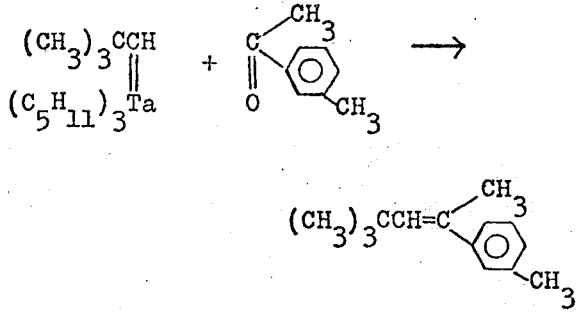

By essentially the method of Example 1, $(C_5H_{11})_3Ta=C_5H_{10}$ was reacted with an equivalent amount of 3-methylacetophenone. After removal of the pentane under reduced pressure, there remained a 3:1 mixture of the cis and trans isomers of 4,4-dimethyl-2-(m-tolyl)-2-pentane. The products were identified by mass spectroscopy and by $^1H$ nmr (in CDCl$_3$): one isomer at τ2.7–2.8 (m,4), τ4.55 (q,1), τ7.66 (s,3), τ8.06 (d,3) and τ9.14 (s,9); the other isomer at τ2.7–2.8, τ4.27, τ7.67, τ7.89, and τ8.80).

If 4-biphenylyl propyl ketone is substituted for 3-methylacetophenone in essentially the procedure of Example 3, the product will be 4-(4biphenyl)-2,2-dimethyl-3-heptene.

EXAMPLE 4

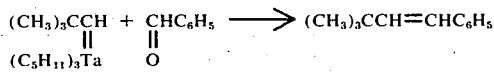

By essentially the method of Example 3, $(C_5H_{11})_3Ta=C_5H_{10}$ was reacted with benzaldehyde to give an approximately 2:1 mixture of the cis and trans isomers of 3,3-dimethyl-1-phenyl-1-butene, which were identified by mass spectroscopy.

Other aldehydes encompassed by the scope of $R^5CHO$ can be used in place of benzaldehyde to give the corresponding ethylenically unsaturated compounds. For example, 1- or 2-napthaldehyde will give the appropriate 3,3-dimethyl-1-naphthyl-1-butene, 3-pyridinecarboxaldehyde will give 3,3-dimethyl-1-(3-pyridyl)-1-butene, and with 2-ethylhexanyl the product will be 5-ethyl-2,2-dimethyl-3-nonene.

EXAMPLE 5

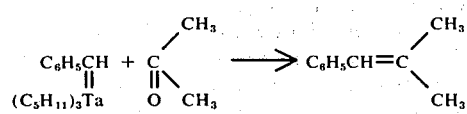

A solution of 2.6 g of $(C_5H_{11})_3TaCl_2$ in 100 ml of hexane was cooled to −78° C, and a solution of 2.4 g of benzyl-(N,N,N',N'-tetramethylethylenediamine) lithium in 30 ml of toluene was added dropwise over one hour with rapid stirring. The mixture was warmed to 25° C, stirred for an additional hour, and filtered, and volatile materials were removed from the deep-orange filtrate under reduced pressure, to give an orange residue that contained trineopentyl(benzylidene)tantalum.

The residue was taken up in 50 ml of pentane, and 0.4 ml of acetone was added. After 15 min the mixture was filtered, and the filtrate was allowed to stand overnight at room temperature. It was then treated with about 20 ml of 1M HCl. Analysis of the organic portion of the product mixture by gas chromatography and mass spectroscopy showed that 2-methyl-1-phenylpropene had been formed.

If t-butyl methyl ketone is used in place of acetone in essentially the foregoing procedure, the product will be 2,3,3-trimethyl-1-phenyl-1-butene. If trineopentyl(1-naphthylmethylene)tantalum is used in place of trineopentyl(benzylidene)tantalum, the product will be 2-methyl-1-(1-naphthyl)-propene.

EXAMPLE 6

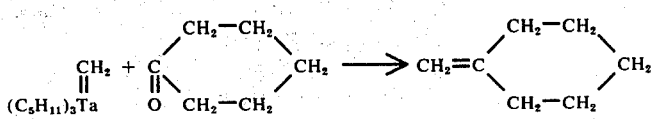

A solution of 1.0 g of trimethyltantalum dichloride and 0.41 g of tantalum pentachloride in 50 ml of toluene was stirred for one hour at room temperature. The resulting solution of methyltantalum tetrachloride was cooled to −78° C, and a solution of 3.15 g of neopentyllithium in 25 ml of ethyl ether was added with stirring over a period of about 20 min. The mixture was warmed to room temperature and filtered, and the solvent was removed from the filtrate under reduced pressure, to give a brown residue that contained trineopentyl(methylene) tantalum, $(C_5H_{11})_3Ta=CH_2$.

The product mixture was dissolved in pentane, 1 ml of cyclohexanone was added, and the mixture was stirred for 5 min. It was then poured into water, and the organic layer was separated and dried over calcium chloride. Methylenecyclohexane was found in the pentane solution by gas chromatography and was identified by mass spectroscopy.

EXAMPLE 7

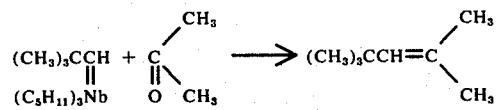

$(C_5H_{11})_3Nb=C_5H_{10}$ was prepared by combining 0.38 g of trineopentylniobium dichloride and 0.16 g of neopentyllithium in pentane at −78° C, allowing the mixture to warm to room temperature, and separating the lithium chloride that was formed by filtration. Acetone (0.0735 ml) was added to the filtrate, whereupon a solid precipitated. The solid was separated by filtration, the volume of the filtrate was reduced to about 1 ml, and the solution was analyzed by gas chromatography. 2,4,4-Trimethyl-2-pentene was found to have been formed in about 31% yield.

EXAMPLE 8

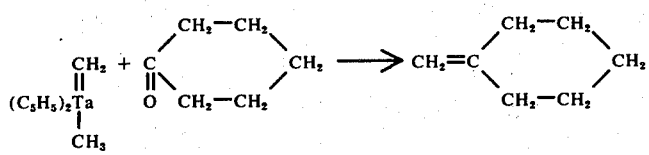

A mixture of 0.34 g of $(C_5H_5)_2Ta(CH_3)=CH_2$ and 2 ml of cyclohexanone was warmed to about 90° C for five minutes four times over a period of six hours. All volatile materials were distilled into a trap under reduced pressure. Methylenecyclohexane was identified in the volatile material by gas chromatography and mass spectrometry.

EXAMPLE 9

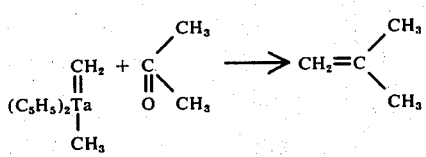

A solution of 0.68 g of dicyclopentadienyl(methyl)-(methylene)tantalum in 5 ml of acetone was kept in a sealed tube overnight at room temperature. Volatile materials were removed under reduced pressure. Gas-chromatographic analysis of the distillate showed that isobutylene had been formed in good yield.

EXAMPLE 10

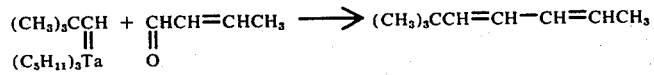

To a solution of 0.464 g of $(C_5H_{11})_3Ta=C_5H_{10}$ in about 5 ml of pentane was added 0.082 ml of crotonaldehyde. A pale solid precipitated immediately, and the characteristic orange color of the $(C_5H_{11})_3Ta=C_5H_{10}$ disappeared. The solid was separated by filtration. Analysis of the filtrate by gas chromatography, mass spectrometry, and nmr showed that approximately equal amounts of trans, cis- and trans, trans-6,6-dimethyl-2,4-heptadiene had been formed.

If 3,5-dimethylcinnamaldehyde is substituted for crotonaldehyde in essentially the foregoing procedure, the product will be 5,5-dimethyl-1-(3,5-xylyl)-1,3-hexadiene.

The ethylenically unsaturated compounds produced by the process of this invention can be oxidized by known methods to the corresponding epoxides, which are useful as monomers and comonomers for conversion to resins and adhesives.

I claim:

1. The process of reacting a metal compound of the formula

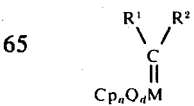

in which

Cp is a π-cyclopentadienyl group having up to one alkyl substituent of 1–10 carbons;

Q is alkyl of 1–10 carbons, aralkyl of 7–10 carbons or diarylmethyl of 13–21 carbons in which the β-carbon is not bonded to hydrogen;

M is niobium or tantalum;

$R^1$ and $R^2$ individually are hydrogen, tertiary alkyl of 4–10 carbons or aryl of 6–10 carbons;

a is 0 or 2;

d is 1 or 3; and a plus d equals 3;

with an organic carbonyl compound of the group consisting of an aldehyde and a ketone, said carbonyl compound being free of Zerewitinoff-active hydrogen and any multiple bond present other than that in the carbonyl group being a carbon to carbon multiple bond or a multiple bond contained in an aromatic heterocyclic ring, at a temperature in the range of 0°–250° C, in the substantial absence of oxygen and moisture, to produce an ethylenically unsaturated compound.

2. The process of claim 1 in which a is 0 and d is 3.

3. The process of claim 1 in which a is 2 and d is 1.

4. The process of claim 1 in which M is niobium.

5. The process of claim 1 in which M is tantalum.

6. The process of claim 1 in which the organic carbonyl compound is an aldehyde.

7. The process of claim 1 in which the organic carbonyl compound is a ketone.

8. The process of claim 1 in which the metal compound is $(C_5H_{11})_3Ta=CHC(CH_3)_3$.

9. The process of claim 1 in which the metal compound is $(C_5H_{11})_3Ta=CHC_6H_5$.

10. The process of claim 1 in which the metal compound is $(C_5H_{11})_3Ta=CH_2$.

11. The process of claim 1 in which the metal compound is $(C_5H_5)_2(CH_3)Ta=CH_2$.

12. The process of claim 1 in which the metal compound is $(C_5H_{11})_3Nb=CHC(CH_3)_3$.

* * * * *

UNITED STATES PATENT OFFICE
CERTIFICATE OF CORRECTION

PATENT NO. : 3,992,472
DATED : November 16, 1976
INVENTOR(S) : Grant Wayne Urry

It is certified that error appears in the above-identified patent and that said Letters Patent are hereby corrected as shown below:

Column 8, line 11, "(4biphenyl)" should be --(4-biphenylyl)--.

Column 8, line 38, "2-ethylhexanyl" should be -- 2-ethylhexanal --.

Signed and Sealed this

Eighth Day of March 1977

[SEAL]

Attest:

RUTH C. MASON
Attesting Officer

C. MARSHALL DANN
Commissioner of Patents and Trademarks